United States Patent
Cruz

(10) Patent No.: US 7,308,896 B2
(45) Date of Patent: Dec. 18, 2007

(54) COMBINATION TRACHEAL HOOK AND SCALPEL DEVICE

(75) Inventor: Rafael Cruz, Clarksville, IN (US)

(73) Assignee: Emergency Medical Devices, Inc., Washington, DC (US)

( * ) Notice: Subject to any disclaimer, the term of this patent is extended or adjusted under 35 U.S.C. 154(b) by 0 days.

(21) Appl. No.: 11/157,702

(22) Filed: Jun. 21, 2005

(65) Prior Publication Data

US 2005/0279363 A1   Dec. 22, 2005

Related U.S. Application Data

(60) Provisional application No. 60/581,816, filed on Jun. 22, 2004.

(51) Int. Cl.
*A61M 16/00* (2006.01)
*A61B 17/34* (2006.01)

(52) U.S. Cl. .................... 128/207.29; 606/185

(58) Field of Classification Search .......... 128/207.29, 128/200.24, 207.14, 200.26; 30/162, 163, 30/151, 2; 606/167, 170, 1, 171, 185, 108; 600/210, 217, 235

See application file for complete search history.

(56) References Cited

U.S. PATENT DOCUMENTS

| | | | | |
|---|---|---|---|---|
| 241,036 A | * | 5/1881 | Lyman .................... | 128/207.29 |
| 338,612 A | * | 3/1886 | Pusey .............................. | 7/118 |
| 2,834,349 A | * | 5/1958 | Springer ...................... | 606/174 |
| 2,991,787 A | | 7/1961 | Shelden et al. | |
| 3,104,666 A | * | 9/1963 | Hale et al. ............. | 128/207.29 |
| 3,306,297 A | | 2/1967 | Voorhees et al. | |
| 3,307,551 A | * | 3/1967 | Violet, Jr. .............. | 128/207.29 |
| 3,759,263 A | * | 9/1973 | Taylor .................... | 128/207.29 |
| 3,863,339 A | * | 2/1975 | Reaney et al. ................. | 30/162 |
| 3,905,101 A | * | 9/1975 | Shepherd ...................... | 30/162 |
| 4,182,337 A | | 1/1980 | Nickson | |
| 4,187,607 A | * | 2/1980 | Simuro et al. ................. | 30/152 |
| 4,285,344 A | * | 8/1981 | Marshall ...................... | 606/174 |
| 4,643,188 A | | 2/1987 | Weiss | |
| 4,877,021 A | | 10/1989 | Higer et al. | |
| 4,889,112 A | | 12/1989 | Schachner et al. | |
| D310,714 S | * | 9/1990 | Dolwick .................... | D24/148 |
| D318,002 S | * | 7/1991 | Loveless ...................... | D7/693 |
| 5,217,007 A | | 6/1993 | Ciaglia | |
| 5,217,476 A | * | 6/1993 | Wishinsky .................. | 606/167 |
| 5,219,354 A | * | 6/1993 | Choudhury et al. ........ | 606/174 |

(Continued)

OTHER PUBLICATIONS

Beers, M.D., Mark H. and Robert Berkow, M.D. (eds.). "Airway Establishment and Control." The Merck of Diagnosis and Therapy. Section 6, Chapter 65. 17th Edition. Accessed Mar. 1, 2006. <http://www.merck.com>.*

(Continued)

*Primary Examiner*—Justine R. Yu
*Assistant Examiner*—Annette Dixon
(74) *Attorney, Agent, or Firm*—Dinsmore & Shohl LLP

(57) ABSTRACT

A portable combination tracheal hook and scalpel device is provided for use in creating an emergency surgical airway in a patient. The device includes a handle and a scalpel portion attached to one end of the handle which includes a blade for creating an incision. The tracheal hook portion includes at least one hook which may be attached directly to the handle, or which may be secured to a sheath which is slidably attached to the handle.

16 Claims, 4 Drawing Sheets

U.S. PATENT DOCUMENTS

| | | | |
|---|---|---|---|
| 5,279,285 A | | 1/1994 | Griggs |
| 5,352,220 A | * | 10/1994 | Abidin et al. .................. 606/1 |
| 5,397,333 A | * | 3/1995 | Knoepfler .................. 606/170 |
| 5,411,512 A | * | 5/1995 | Abidin et al. ............... 606/167 |
| 5,527,329 A | | 6/1996 | Gharibian |
| 5,558,081 A | | 9/1996 | Lipkin |
| 5,662,669 A | | 9/1997 | Abidin et al. |
| 5,988,168 A | * | 11/1999 | Bair ...................... 128/207.29 |
| 2004/0103900 A1 | | 6/2004 | Melker et al. |

OTHER PUBLICATIONS

Gomersall, Charles. "Ciaglia." The Chinese University of Hong Kong: Department of Anesthesia and Intesive Care. 2006. Chinese University of Hong Kong. Accessed: Sep. 11, 2006 <http://www.aic.cuhk.edu.hk/web8/Ciaglia.htm>.*

Jurasek, Gale. "Tracheostomy at Your Fingertips." Pulmonary Reviews.com. vol. 9, No. 11, Nov. 2004. Johnson Publishing. Accessed: Sep. 11, 2006 <http://www.pulmonaryreviews.com/nov04/pr_nov04_tracheostomy.html>☐☐.*

Cheng, Ka-Shun and Ju-Mei Ng. "Airway loss during tracheostomy" Correspondence to the Canadian Journal of Anesthesia 49:110 (2002). Canadian Anesthesiologists' Society, 2002. Accessed Sep. 11, 2006. <http://www.cja-jca.org/cgi/content/full/49/1/110>.*

G. & C. Merriam Co. "Handle." Webster's New Collegiate Dictionary. G. & C. Merriam Co. 1977.*

* cited by examiner

COMBINATION TRACHEAL HOOK AND SCALPEL DEVICE

CROSS REFERENCE TO RELATED APPLICATIONS

This application claims the benefit of U.S. Provisional Application No. 60/581,816, entitled TRACHEAL HOOK AND SCALPEL COMBINATION, filed Jun. 22, 2004. The entire contents of said application are hereby incorporated by reference.

BACKGROUND OF THE INVENTION

The present invention relates to a surgical instrument for use in performing emergency surgical airway or cricothyrotomies/tracheostomies, and more particularly to a combination tracheal hook and scalpel device which can be easily stored in a pocket or is otherwise readily accessible.

When the laryngeal opening of a patient becomes obstructed, blocking the flow of air to the lungs, an emergency surgical airway must be created to relieve the obstruction. In addition, when the laryngeal opening cannot be visualized (for normal intubation) because of the presence of blood or vomit, an emergency surgical airway is often necessary to save the patient. This procedure is commonly referred to as a cricothyrotomy or tracheostomy. Techniques for performing an emergency surgical cricothyrotomy/tracheostomy vary, but generally, the technique is a multi-step procedure that requires the use of a scalpel for creating an incision, a dilation instrument, and a tracheal hook for stabilizing the larynx. The group of surgical instruments used to create the surgical airway are often collectively included in a surgical airway kit or surgical airway instrument tray.

Although such kits are effective at providing the tools necessary to perform a cricothyrotomy/tracheostomy, currently available kits have several problems. One problem is that surgical airway kits are neither compact nor easily portable. For example, because the kits include multiple instruments, they can be bulky and are not easily carried by a doctor or other critical care practitioner on their person. Accordingly, when an emergency surgical airway must be provided, a kit must be located, a process that takes up valuable time, and under the circumstances, may be life threatening.

Another problem with currently available surgical kits is that effective use of a particular kit requires a high degree of familiarity with each individual surgical instrument and a high degree of familiarity with the cricothyrotomy/tracheostomy technique that the kit is designed for performing.

A number of devices have been developed in an attempt to combine several surgical instruments into one device which can be used to perform a cricothyrotomy. See, for example, U.S. Pat. No. 5,988,168, which teaches an apparatus including a pair of handles with hooked ends which can be mated with a scalpel. However, such devices are relatively large in size and are too cumbersome to be easily carried by a physician or other medical personnel.

Accordingly, there is still a need in the art for an improved method of performing a cricothyrotomy/tracheostomy in an emergency situation which provides a medical device for performing the procedure in a compact and/or portable manner, and which device is simple to use and operate.

SUMMARY OF THE INVENTION

Embodiments of the present invention meet that need by providing a portable combination tracheal hook and scalpel device which may be used to create an emergency surgical airway in a patient in a fast, effective manner.

According to one aspect of the invention, a combination tracheal hook and scalpel device for providing a surgical airway in a patient is provided which comprises a handle having first and second ends, a scalpel portion attached to the first end of the handle which comprises a blade for creating an incision, and a tracheal hook portion attached to the handle, which tracheal hook portion comprises at least one hook. The combination tracheal hook and scalpel device is compact and portable. By "portable," it is meant that the device is about the size of a pocket pen and may be easily carried by a physician, such as in a pocket.

In a preferred embodiment of the invention, the device preferably further includes a sheath for enclosing the scalpel portion when it is not in use. The sheath is preferably slidably attached to the handle. The handle preferably includes one or more grooves therein for slidably receiving the sheath.

In one embodiment of the invention, the tracheal hook portion is attached to the sheath. Preferably, the tracheal hook portion is integral with the sheath. Alternatively, the tracheal hook portion may be attached directly to the handle. In this embodiment, the handle preferably includes a groove therein for slidably receiving the tracheal hook portion. If desired, the tracheal hook portion may include a locking mechanism to allow it to be locked into position along the handle.

In another embodiment of the invention, the tracheal hook portion of the device comprises at least two hooks. Preferably, the tracheal hook portion comprises first and second hooks, where the first hook preferably is positioned at the first end of the handle and the second hook is positioned at the second end of the handle. Where the hooks are positioned at opposite ends of the handle, at least one of the hooks preferably functions as a handle to facilitate movement of the tracheal hook portion along the handle. Alternatively, the first and second hooks may both be positioned at the first end of the handle.

In yet another embodiment of the invention, the scalpel portion and/or the tracheal hook portion of the device is retractable, i.e., the scalpel portion and/or tracheal hook portion may be retracted within the handle when one or the other portion is not in use. In this embodiment, the handle may include a button or other mechanism to release the scalpel blade or tracheal hook for retraction into the handle.

The present invention also provides a method of establishing a surgical airway in a patient using the portable combination tracheal hook and scalpel device which includes making an incision through the cricoid membrane or trachea of the patient using the scalpel portion; inserting the tracheal hook into the incision; rotating the hook so that it attaches to the lower cricoid cartilage of the patient and applying upward and caudal traction to open the incision; and placing an endotracheal tube into the airway.

Preferably, the method includes inserting a finger into the incision and into the trachea, allowing palpation of the tracheal rings to establish correct placement of the endotracheal tube. The combination tracheal hook and scalpel device is simple to operate and allows a cricothyrotomy/tracheostomy to be performed rapidly.

Accordingly, it is a feature of embodiments of the present invention to provide a portable combination tracheal hook and scalpel device for providing a surgical airway in a patient. Other features and advantages of the invention will be apparent from the following description, the accompanying drawings, and the appended claims.

DETAILED DESCRIPTION OF THE PREFERRED EMBODIMENTS

Figure 1A:
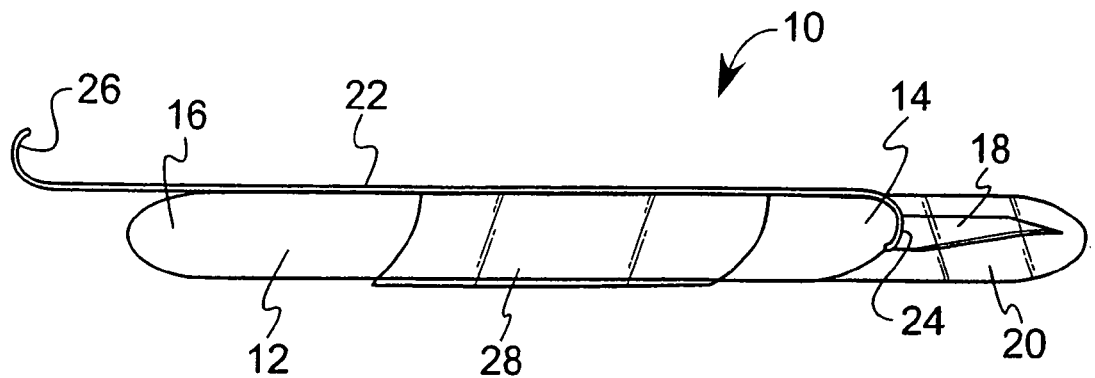
FIG. 1A is a side view of one embodiment of the combination tracheal hook and scalpel device of the present invention.

Reference is now made to FIG. 1A, which illustrates one embodiment of the combination tracheal hook and scalpel device of the present invention. The combination 10 includes a handle 12 having first and second ends 14 and 16, and a scalpel portion 18 comprising a blade at the first end 14 of the handle. If desired, the scalpel portion may include an optional removable cap 20 which encloses the scalpel portion when it is not in use.

Figure 1B:
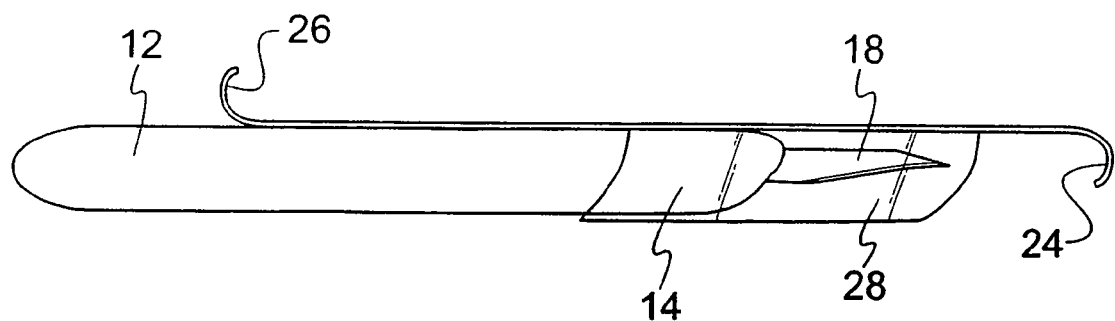
FIG. 1B is a side view of the embodiment of FIG. 1 shown with the scalpel portion enclosed by a sheath.

The device further includes a tracheal hook portion 22 which is attached to the handle 12. In the embodiment shown, the tracheal hook portion comprises first and second hooks 24 and 26, where the first hook 24 is positioned at the first end of the handle 14 and the second hook 26 is positioned at the second end 16 of the handle. The tracheal hook portion is preferably attached to a sheath 28 which is slidably attached to the handle of the device. As shown in FIG. 1B, the sheath may be slid along the length of the handle such that the sheath encloses the scalpel when the tracheal hook portion 24 is in use.

Figure 2:
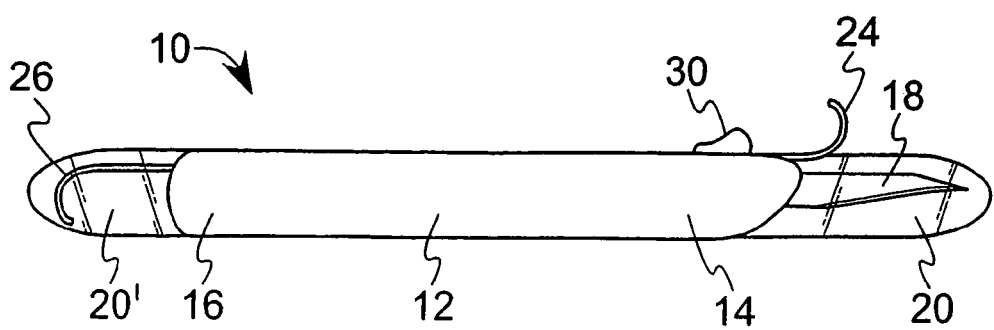
FIG. 2 is a side view of an alternative embodiment of the combination tracheal hook and scalpel device.

In an alternative embodiment of the invention illustrated in FIG. 2, the combination hook and scalpel device 10 includes a scalpel portion 18 at a first end 14 of the handle and a tracheal hook portion comprising first and second hooks 24 and 26, where the second hook 26 is integral with the handle. As shown, both the scalpel portion and the hook 26 may be covered with optional caps 20, 20' when not in use. In this embodiment, an optional scalpel retraction lever 30 is further included on the outer portion of the handle for retracting the scalpel portion 18 when it is not in use.

Figure 3A:
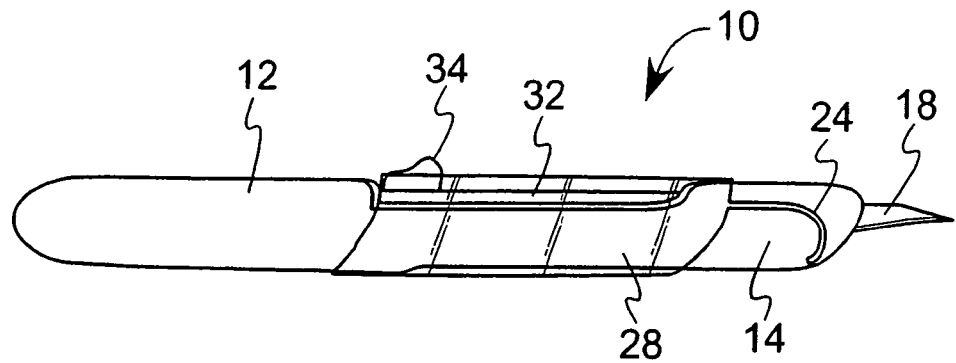
FIG. 3A is a side view of another alternative embodiment of the combination tracheal hook and scalpel device.
Figure 3B:
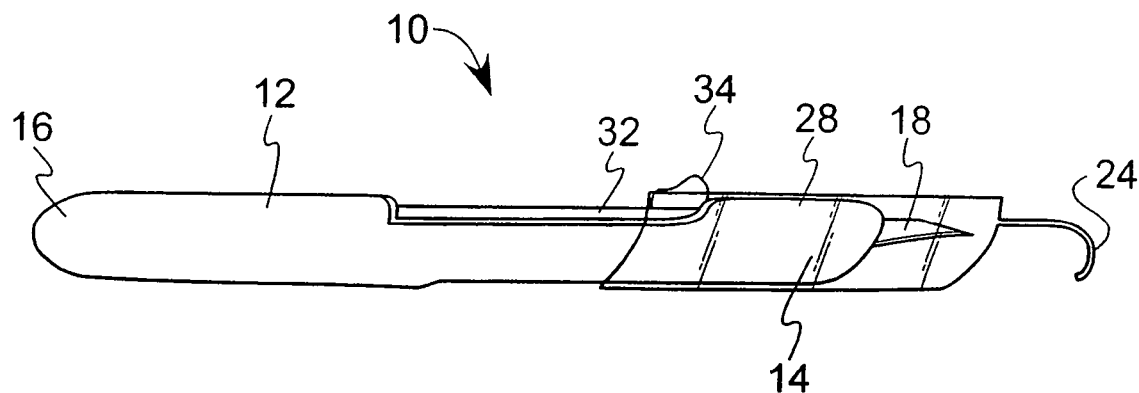
FIG. 3B is a side view of the embodiment of FIG. 3A shown with the scalpel portion enclosed by a sheath.

FIGS. 3A and 3B illustrate yet another embodiment of the invention in which both the scalpel portion 18 and the tracheal hook portion 24 are positioned at the first end 14 of the handle 12. In the embodiment shown, the tracheal hook portion is attached to a sheath 28 which is slidably attached to the outer portion of the handle. Preferably, the tracheal hook portion is formed integrally with the sheath. In this embodiment, the handle 12 includes a groove 32 therein for slidably receiving and engaging the sheath, and preferably further includes a notch 34 which, when pressed and released, allows the sheath to be locked into a desired position. For example, when the scalpel portion is in use as shown in FIG. 3A, the notch is pressed, allowing the sheath to be lowered and locked into place such that the scalpel portion 18 is exposed. When the tracheal hook portion is in use as illustrated in FIG. 3B, the sheath is raised and locked into position so that the scalpel portion is enclosed by the sheath and the hook 24 extends outward beyond the end of the scalpel portion.

Figure 4:
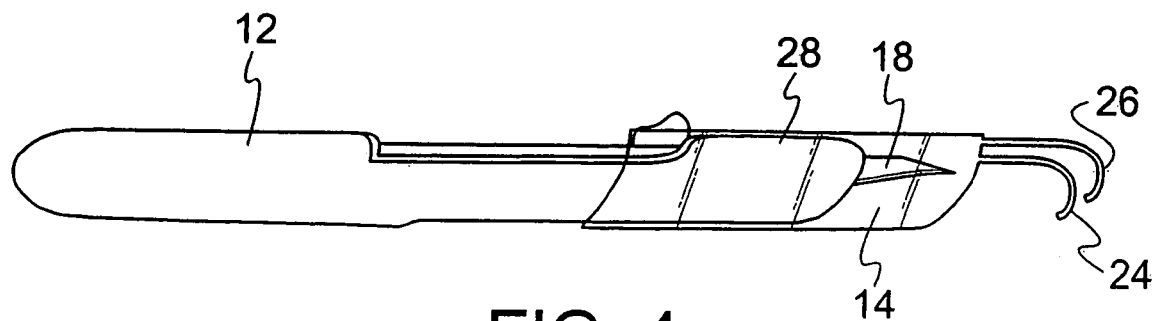
FIG. 4 is a side view of another embodiment of the device which includes two tracheal hooks at the same end of the handle.

FIG. 4 illustrates yet another embodiment of the combination tracheal hook and scalpel device in which the tracheal hook portion comprises two hooks 24, 26 at the first end 14 of the handle. The hooks are preferably attached to the sheath 28. While the invention has been shown with the use of one or two tracheal hooks, it should be appreciated that multiple hooks may be employed in the device. For example, in the embodiment shown in FIG. 4, a third hook (not shown) may be included at the second end of the handle, similar to the embodiment shown in FIGS. 1 and 2. Further, it should be appreciated that while the tracheal hook portion has been shown as being integral with the handle or attached to a sheath which slides over the handle, it may also be formed on or extending from the inner portion of the handle similar to the scalpel portion. It should also be appreciated that in embodiments where the tracheal hook portion comprises two or more hooks at opposite ends of the handle, one of the hooks (for example, hook 26 as shown in FIG. 1A/1B) preferably functions as a "handle" which facilitates placement of a finger to facilitate movement of the hook along the handle.

Figure 7:
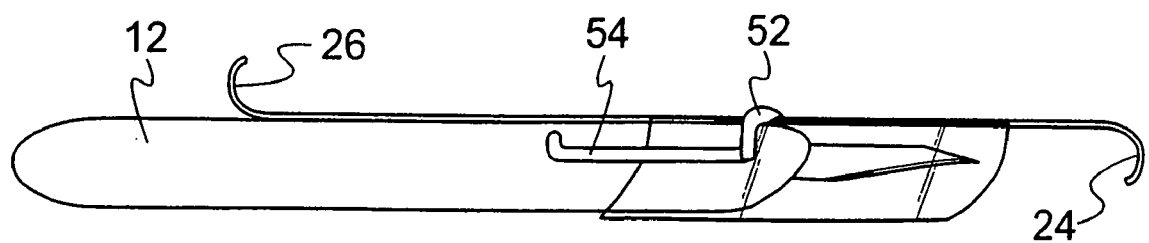
FIGS. 7 and 8 are side views illustrating another embodiment of the combination tracheal hook and scalpel device.
Figure 8:
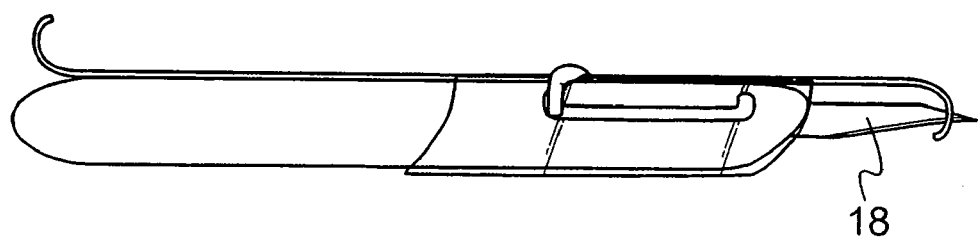

Another alternative embodiment of the invention is shown in FIGS. 7 and 8 in which the tracheal hook portion is attached directly to the handle and is slidable along the length of the handle by the use of a notch or other device 52 which engages a groove 54 along the handle. In this embodiment, a slidable sheath 28 may still be used to cover the scalpel portion when it is not in use. As shown in FIG. 8, when it is desirable to use the scalpel portion 18, the hook portion 24 and sheath may be slid down the length of the handle to expose the scalpel.

Figure 9:
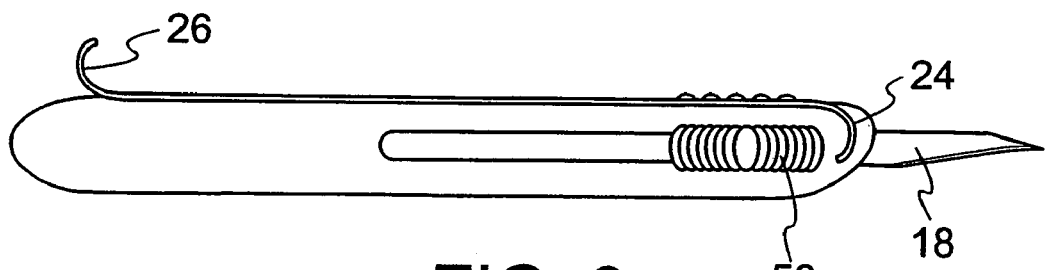
FIGS. 9 and 10 are side views illustrating another embodiment of the combination tracheal hook and scalpel device.
Figure 10:
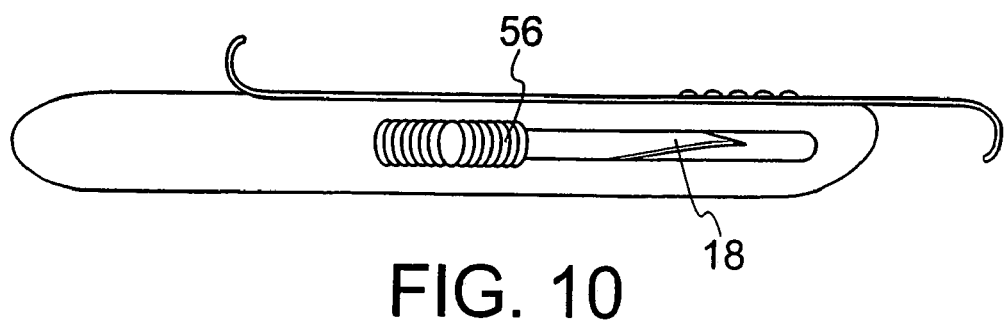

Yet another alternative embodiment of the invention is illustrated in FIGS. 9 and 10 in which the tracheal hook portion and/or the scalpel portion are retractable from the handle, depending on which is in use. As illustrated in FIG. 9, the tracheal hook portion 24 is retracted by sliding the hook portion along a groove in the handle (not shown), and in FIG. 10, the scalpel is retracted by pushing and sliding button 56. Also as shown, the tracheal hook portion may include grooves or ridges which enable a user to grip the hook portion as it is slid along the length of the handle. Such grooves, ridges, or other means such as a rubber coating may be provided on any portion of the handle or tracheal hook portion to facilitate easy gripping and use of the device.

Figure 5:
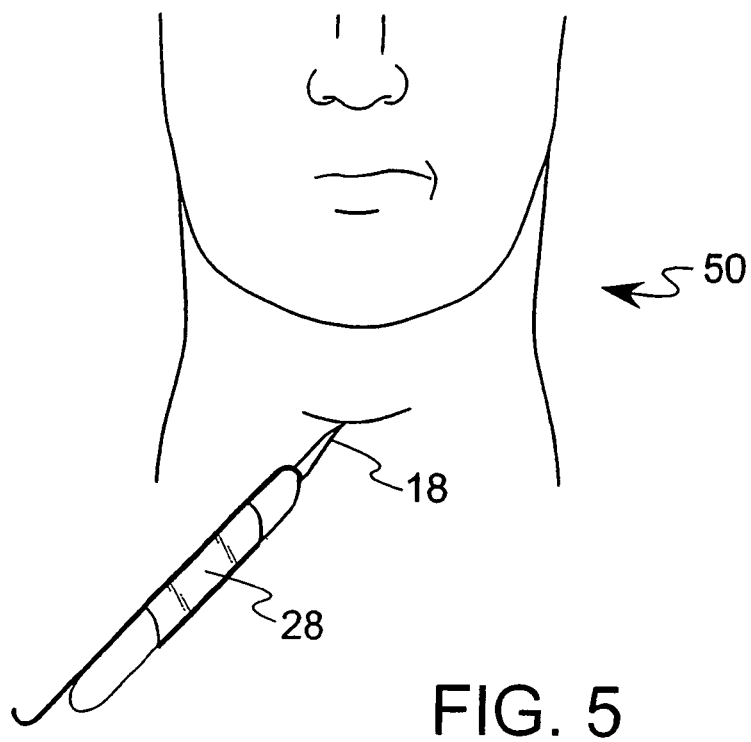
FIGS. 5 and 6 illustrate a method of performing a cricothyrotomy using the combination tracheal hook and scalpel device shown in FIGS. 3A and 3B.
Figure 6:
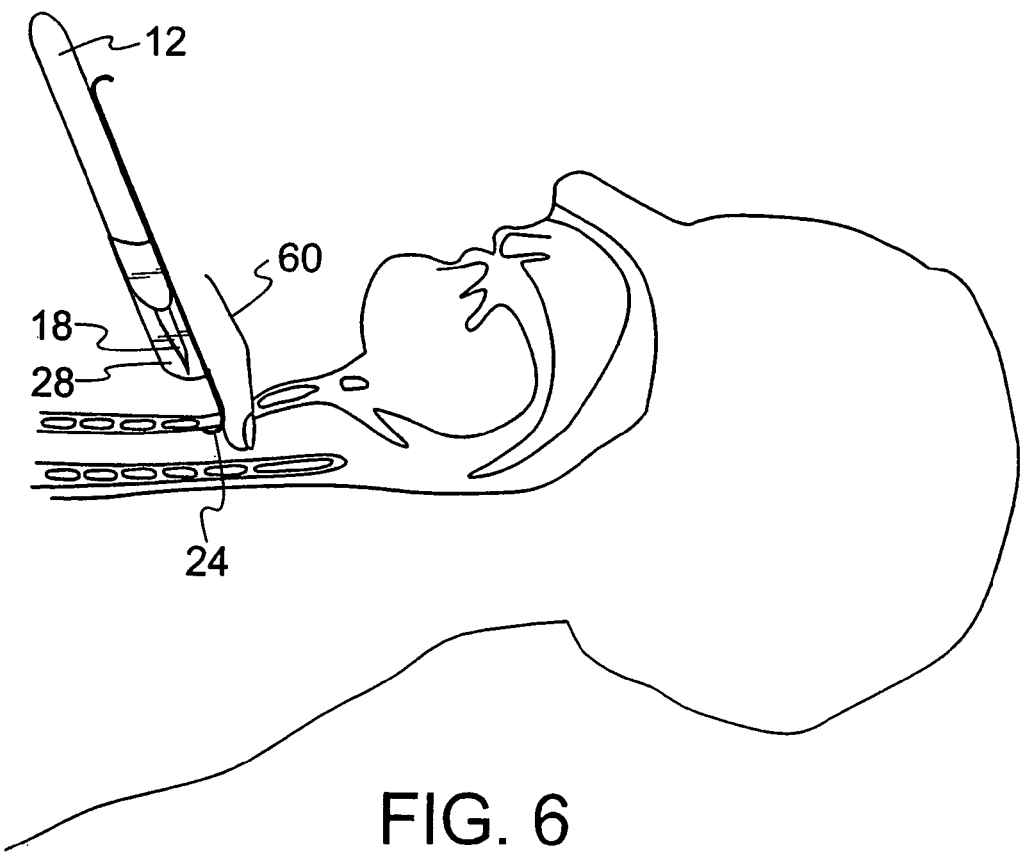

Referring now to FIGS. 5 and 6, an exemplary cricothyrotomy procedure in accordance with the present invention is diagrammatically shown utilizing the embodiment of the combination tracheal hook and scalpel device shown in FIGS. 1A and 1B. Referring to FIG. 5, the scalpel portion 18 is exposed and is used to create an incision through the cricoid membrane of a patient 50. After the incision has been made, the sheath 28 is slidably moved along the handle using notch 34 so that the scalpel portion 18 is now enclosed by the sheath 28 and the tracheal hook portion comprising hook 24 is now inserted into the incision as illustrated in FIG. 6. The hook is then rotated about 90 degrees so that it attaches to the lower cricoid cartilage of the patient. Upward and caudal traction is then applied to further open the incision such that a physician or other practitioner can then insert a finger 60 into the incision and open the palpating tracheal rings of the patient to establish proper placement of an endotracheal tube which completes the formation of an airway.

The combination tracheal hook and scalpel device is easy to use and operate and because it is relatively small in size (about the size of a large pen), it is easy to carry in a pocket or the like for easy retrieval and use.

Having described the invention in detail and by reference to preferred embodiments thereof, it will be apparent that modifications and variations are possible without departing from the scope of the invention.

The invention claimed is:

1. A combination tracheal hook and scalpel device for providing a surgical airway in a patient comprising:
    a handle having first and second ends;
    a scalpel portion attached to said first end of said handle; said scalpel portion comprising a blade for creating an incision; and
    a tracheal hook portion permanently attached to said handle and positioned at said first end of said handle; said tracheal hook portion comprising at least one hook, which, when in use, extends beyond the outermost portion of said first end of said handle for engagement with the cartilage of a patient; wherein said device is portable and includes a sheath that is slidably attached to said handle.

2. The device of claim 1 further including a sheath for enclosing said scalpel portion.

3. The device of claim 2 wherein said tracheal hook portion is attached to said sheath.

4. The device of claim 2 wherein said tracheal hook portion is integral with said sheath.

5. The device of claim 1 wherein said sheath can be locked into position.

6. The device of claim 1 wherein said handle includes a groove therein for slidably receiving said sheath.

7. The device of claim 1 wherein said handle includes a groove therein which allows said tracheal hook portion to be slidably retracted from said handle.

8. The device of claim 1 wherein said tracheal hook portion is integral with said handle.

9. The device of claim 1 wherein said tracheal hook portion comprises at least two hooks.

10. A combination tracheal hook and scalpel device for providing a surgical airway in a patient comprising:
    a handle having first and second ends;
    a retractable scalpel portion attached to said first end of said handle; said scalpel portion comprising a blade for creating an incision; and
    a retractable tracheal hook portion permanently attached to said handle and positioned at said first end of said handle;
    wherein when said scalpel portion is in use, said tracheal hook portion is retracted; and when said tracheal hook portion is in use, said scalpel portion is retracted and wherein said device further includes a sheath which is slidably attached to said handle.

11. The device of claim 10 wherein said tracheal hook portion comprises at least two hooks.

12. A method of establishing a surgical airway in a patient comprising:
    providing a portable combination tracheal hook and scalpel device comprising a a handle having first and second ends; a scalpel portion comprising a blade attached to said first end of said handle; and a tracheal hook portion comprising at least one hook permanently attached to said handle and positioned at the first end of said handle and wherein said device further includes a sheath which slidably attached to said handle;
    making an incision through the cricoid membrane of the patient using said scalpel portion;
    extending said tracheal hook portion so that it extends beyond the outermost portion of said first end of said handle and inserting said tracheal hook into said incision;
    rotating said hook so that it attaches to the lower cricoid cartilage of the patient and applying upward and caudal traction to open said incision; and
    placing an endotracheal tube into an airway of the patient.

13. The method of claim 12 including inserting a finger into said incision and palpating the tracheal rings of the patient to establish placement of said endotracheal tube.

14. The method of claim 12 wherein said tracheal hook portion is secured to said sheath.

15. The method of claim 12 wherein said sheath covers said scalpel portion when said tracheal hook portion is in use.

16. The device of claim 12 wherein said tracheal hook portion comprises at least two hooks.

* * * * *